Jan. 16, 1973 M. B. WAKEFIELD Plant Pat. 3,296
DOGWOOD TREE
Filed April 30, 1971
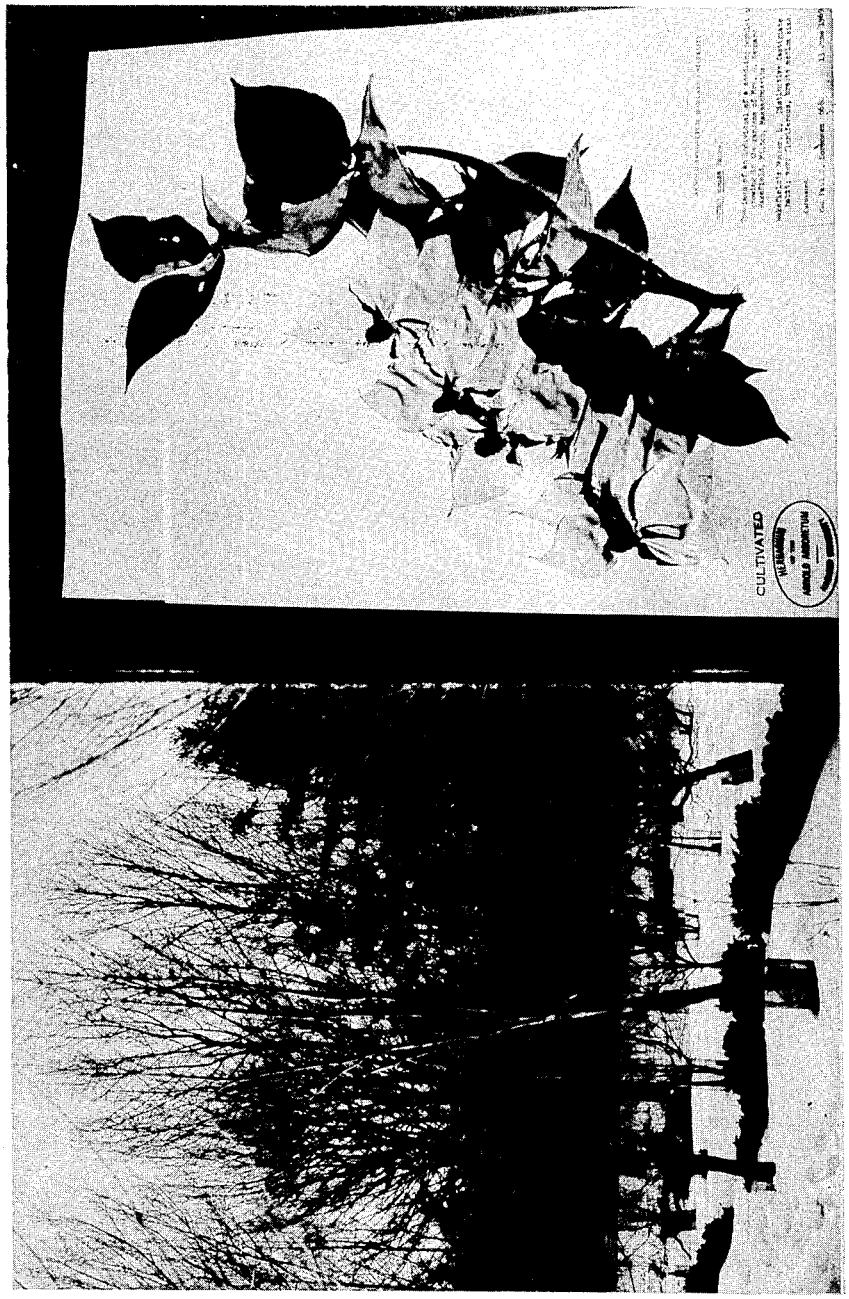
Inventor.
M. B. Wakefield
By: Robb & Robb
Attorneys.

United States Patent Office

Plant Pat. 3,296
Patented Jan. 16, 1973

3,296

DOGWOOD TREE

Mary B. Wakefield, 1465 Brush Hill Road,
Milton, Mass. 02186

Filed Apr. 30, 1971, Ser. No. 138,968
Int. Cl. A01h 5/12
U.S. Cl. Plt.—51 1 Claim The present invention relates to a new and distinct variety of dogwood tree of the Japanese dogwood type botanically known as *Cornus kousa,* which was originated by me from a seed which was initially processed and planted by me indoors, and then set out as a young seedling plant in my nursery located at Milton, Mass.

When I acquired this seed, I was attending classes on plant propagation, as conducted at the Arnold Aboretum which is near my home in Milton, Mass. My interest in plant propagation and experimentation led me to seek and receive permission to obtain seeds of various plants, including dogwoods, being grown at the Arnold Arboretum. This particular seed was one of many which was taken by me from a dogwood tree specimen of the *kousa* type which had attracted my attention at the Arboretum aforementioned, but which was of uncertain origin and parentage. In a few years after setting out and observing this seedling in my nursery, I noticed that its form differed considerably from the others and from all other dogwoods typical of the *kousa* species with which I and the experts at the Arnold Arboretum were familiar, in that the new seedling exhibited a fastigiate and distinctly upright habit of growth. I, therefore, kept this seedling under close observation, and in due course, I asexually reproduced the same in my nursery by means of rooted cuttings taken therefrom.

Continued and prolonged testing and observations of the original seedling and its progeny derived from the rooted cuttings have conclusively demonstrated that their fastigiate habit comes true and is stable, among other distinctive and unusual features. I am accordingly convinced that my new seedling represents a new and improved dogwood variety which is distinguished from its parent, as well as from all other dogwood varieties, as evidenced by the following unique combination of principal characteristics which are outstanding therein:

(1) A fastigiate and distinctly upright habit of growth, with the trunk dividing, beginning well above the ground, and each division continuing to ascend and bearing numerous short horizontal branches which turn upward at their tips;

(2) Distinctive and attractive, large white flowers, each having four broadly over-lapping bracts, with the two upper bracts being slightly narrower than the two lower bracts, and the flowers being borne all along the numerous horizontal branches which are so densely twigged that the flowers are quite close together and appear in vertical series as narrow white tiers which is quite unusual and attractive;

(3) Attractive large fruit of somewhat blocky shape and which are green in color at the beginning, then become yellow, and finally turn red quite early as the fruiting season progresses;

(4) Excellent hardiness to at least −20° F. without injury; and (5) Especial suitability for accent use along sidewalks and near buildings, and for street, park, patio and garden plantings.

The accompanying drawing shows a typical young bare tree specimen of my new dogwood variety which is illustrative of its fastigiate habit of growth, and also shops on a larger scale herbarium specimens of typical flowers and foliage as borne on a short section of a typical branch during the flowering season.

The following is a detailed description of my new dogwood variety, with color terminology in accordance with the Royal Horticultural Colour Chart, published by the Royal Horticultural Society of London, except where general color terms of orginary dictionary significance are obvious:

Breeding: A seedling of an unnamed and unpatented variety of the species *C. kousa* of uncertain origin and parentage.

Propagation: Holds its distinguishing characteristics through succeeding propagations by rooted cuttings.

Locality where grown and observed: Milton, Mass.

Tree: Small; fastigiate (upright); tall; hardy to at least −20° F.

*Trunk.*—Smooth.

*Branches.*—Slender; smooth. Color—bottom of twigs—Grey-Brown, Plate 199 A. Top of twigs—Grey, Plate 201 B.

*Leaves.*—Quantity—abundant. Size—length—from about 3¾ inches to 4¼ inches. Width—from about 2 inches to 2⅜ inches.

*Shape.*—Elliptic ovate, with caudate tip.

*Color.*—Vegetative buds—Grey, Plate 201 A. Mature—Yellow-Green, Plate 144 A. Autumn—Grey-Red, Plate 181 C.

*Margin.*—Obscurely crenate.

*Petiole.*—Medium length; from about ¼ inch to ⅜ inch long.

Flower buds:

*Hardiness.*—Hardy to at least −20° F.

*Size.*—Length—from about ¾ inch to 5/16 inch. Width—from about 5/32 inch to 3/16 inch.

*Shape.*—Broadly fusiform.

*Color.*—Brown, Plate 200 D.

Flowers (Inflorescence):

*Dates of first and full bloom.*—About June 1 and June 15, respectively, at Milton Mass.

*Quantity.*—Abundant.

*Size.*—Large; many exceed 5½ inches in diameter.

*Petalage (bracts).*—Number of bracts—4. Shape—from elliptic to ovate, with caudate tips. Size—length—from about 2 7/16 inches to 2⅝ inches or more. Width—from about 2⅛ inches to 2¼ inches or more.

*Color.*—Good white when mature.

Fruit:

*Size.*—Up to 1½ inches in diameter.

*Color.*—Yellow-Green, Plate 144 A at first, becoming Yellow, Plate 10, and then turning to Red, Plate 45 A at end of season.

General observations: While the fastigiate habit of my new dogwood variety is its most outstanding characteristic, its unusually large, well-shaped flowers and their unique arrangement which give them the appearance of a vertical series of narrow, white tiers, together with its large and attractively colored fruit, make this variety one of the most beautiful, unique and valuable of all the Japanese dogwoods I have ever seen.

I claim:

1. A new and distinct variety of dogwood tree of the Japanese dogwood type, substantially as herein shown and described, characterized particularly as to novelty by the unique combination of a fastigiate and distinctly upright habit of growth, with the trunk dividing, beginning well above the ground, and each division continuing to ascend and bearing numerous short horizontal branches which turn upward at their tips, distinctive and attractive, large white flowers, each having four broadly overlapping bracts, with the two upper bracts being slightly narrower than the two lower bracts, and the flowers being borne all along the numerous horizontal branches which are so densely twigged that the flowers are quite close together and appear in vertical series as narrow white tiers which is quite unusual and attractive, attractive large fruit of somewhat blocky shape and which are green in color at the beginning, then become yellow, and finally turn red quite early as the fruiting season progresses, excellent hardiness to at least —20° F. without injury, and especial suitability for accent use along sidewalks and near buildings, and for street, park, patio and garden plantings.

No references cited.

ROBERT E. BAGWILL, Primary Examiner